(12) United States Patent
Adamy

(10) Patent No.: US 6,355,229 B1
(45) Date of Patent: Mar. 12, 2002

(54) ORAL COMPOSITION CONTAINING CETYLPYRIDINIUM CHLORIDE AND GUAR HYDROXYPROPYLTRIMONIUM CHLORIDE AND METHOD OF USING THE SAME

(75) Inventor: Steven T. Adamy, Hamilton, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 09/893,766

(22) Filed: Jun. 27, 2001

(51) Int. Cl.[7] ............... A61K 7/16; A61K 7/22; A61K 9/20; A61K 9/68

(52) U.S. Cl. ............... 424/54; 424/48; 424/49; 424/435; 424/440; 424/464

(58) Field of Search ............... 424/48, 49, 54, 424/435, 440, 464

(56) References Cited

U.S. PATENT DOCUMENTS

| | | | |
|---|---|---|---|
| 4,389,394 A | | 6/1983 | Drucker |
| 4,405,654 A | | 9/1983 | Lee |
| 4,585,650 A | * | 4/1986 | Newberry et al. ............ 424/73 |
| 4,839,158 A | | 6/1989 | Michaels |
| 4,847,076 A | * | 7/1989 | Deshpande et al. ...... 424/70.13 |
| 4,971,797 A | | 11/1990 | Cherukuri |
| 5,013,763 A | * | 5/1991 | Tubesing et al. ...... 424/195.18 |
| 5,037,643 A | * | 8/1991 | Green ............... 424/78.23 |
| 5,076,953 A | * | 12/1991 | Jordan et al. ............ 510/151 |
| 5,085,857 A | * | 2/1992 | Reid et al. ............ 424/70.12 |
| 5,152,914 A | * | 10/1992 | Forster et al. ............ 510/122 |
| 5,158,763 A | | 10/1992 | Gaffar et al. |
| 5,370,881 A | | 12/1994 | Fuisz |
| 5,374,638 A | | 12/1994 | Hauschild |
| 5,376,360 A | | 12/1994 | Domke et al. |
| 5,523,079 A | * | 6/1996 | Gough ............ 424/70.11 |
| 5,622,689 A | | 4/1997 | Lukacovic |
| 5,801,116 A | * | 9/1998 | Cottrell et al. ............ 502/404 |
| 5,849,268 A | | 12/1998 | Lukacovic |
| 5,849,271 A | | 12/1998 | Lukacovic |
| 5,948,390 A | | 9/1999 | Nelson et al. |
| 6,274,128 B1 | * | 8/2001 | Bergmann et al. ......... 424/70.1 |

FOREIGN PATENT DOCUMENTS

| | | |
|---|---|---|
| EP | 0 009 408 A1 | 4/1980 |
| EP | 0 422 803 A2 | 4/1991 |
| EP | 0 480 811 A2 | 4/1992 |
| EP | 0 507 598 A1 | 10/1992 |
| EP | 0 920 857 A2 | 6/1999 |
| WO | WO 90/15592 | 6/1990 |
| WO | WO 97/46217 | 12/1997 |

* cited by examiner

Primary Examiner—Shep K. Rose
(74) Attorney, Agent, or Firm—Irving M. Fishman

(57) ABSTRACT

An oral composition comprises an antibacterial effective amount of cetylpyridinium chloride, an effective amount of guar hydroxypropyltrimonium chloride, sufficient to bind to compounds which undesirably bind to cetylpyridinium chloride thereby enabling the cetylpyridinium chloride to effectively bind to tooth surfaces and perform an antibacterial function, and an orally acceptable carrier.

20 Claims, No Drawings

ORAL COMPOSITION CONTAINING CETYLPYRIDINIUM CHLORIDE AND GUAR HYDROXYPROPYLTRIMONIUM CHLORIDE AND METHOD OF USING THE SAME

FIELD OF THE INVENTION

The present invention relates to oral compositions containing cetylpyridinium chloride as an active antibacterial agent which may be used to inhibit formation of plaque, oral malodor, gingivitis, periodontal disease and the like. The oral composition contains the active agent and an effective amount of guar hydroxypropyltrimonium chloride which enables the active agent to more effectively bind to tooth surfaces to perform its antibacterial function.

BACKGROUND OF THE INVENTION

Cetylpyridinium chloride (CPC) is well known as an antibacterial agent especially for the inhibition of plaque formation. This antibacterial agent has been used in commercial mouthwash products such as Scope® and Cepacol® and several other types of oral care products. The environment of such commercial mouthwash products enables cetylpyridinium chloride to freely contact those oral surfaces which may harbor unwanted microorganisms. These microorganisms contribute to both the initiation and progression of gingivitis, plaque, periodontal disease, and/or breath malodor in the oral cavity of warm-blooded animals. Such conditions are usually treated by reducing the presence of the microorganisms in the oral cavity through the use of dental care products containing antibacterial agents including cetylpyridinium chloride.

The antibacterial activity of cetylpyridinium chloride is, without being bound to the theory, believed to be linked to the cationic charge of its amine group. Thus, cetylpyridinium chloride is attracted to and binds to negatively-charged protein moieties on the cell membrane or cell wall of the microorganism and to tooth surfaces which are also typically negatively charged. The resulting attachment to microorganisms disrupts the cell wall structure causing leakage of the intracellular fluids, eventually killing the associated microorganism. However, cetylpyridinium chloride is generally not effective in many systems because of its tendency to complex with components that carry a negative charge. When bound to negatively charged particles in this manner, cetylpyridinium chloride is unavailable for effective contact with tooth surfaces and microorganisms, thereby rendering the active agent ineffective for its intended purpose.

For this reason, cetylpyridinium chloride has not been totally effective in typical oral care products for the treatment and/or prevention of gingivitis, plaque, periodontal disease, and/or breath malodor. For example, toothpaste compositions typically include anionic surfactants and artificial sweetening agents. These components of toothpaste compositions typically bind to cetylpyridinium chloride and thereby render the same ineffective or substantially less effective as an antibacterial agent. Other components typically found in a toothpaste composition such as abrasives also bind to cetylpyridinium chloride. Accordingly, the use of cetylpyridinium chloride in toothpaste compositions has been problematic. Even in commercial mouthwash products that contain cetylpyridinium chloride, the availability of cetylpyridinium chloride at tooth surfaces is very low and therefore its antibacterial effectiveness is limited.

It would be an advance in the art of oral compositions if such compositions contain an effective amount of cetylpyridinium chloride in which antibacterial activity is not materially diminished by the presence of other components which tend to bind to the active agent.

SUMMARY OF THE INVENTION

The present invention is generally directed to an oral composition in which cetylpyridinium chloride is present as an antibacterial agent as part of an effective oral hygiene program. In a particular aspect of the present invention, there is provided an oral composition comprising:

a) an antibacterial effective amount of cetylpyridinium chloride;
  b) an effective amount of guar hydroxypropyltrimonium chloride sufficient to bind to compounds which undesirably bind to cetylpyridinium chloride thereby enabling the cetylpyridinium chloride to effectively bind to tooth surfaces and perform an antibacterial function; and
  c) an orally acceptable carrier.

The invention further relates to a method of reducing the presence of microorganisms in an oral cavity of a warm-blooded animal, the method comprising administering to the oral cavity an effective amount of the above oral composition.

DETAILED DESCRIPTION OF THE INVENTION

The present invention relates to compositions and methods of reducing the presence of microorganisms in an oral cavity of a warm-blooded animal in the course of treating and/or preventing breath malodor, and diseases of the oral cavity (e.g. plaque, gingivitis, periodontal disease) in the warm-blooded animal, by topically applying to the oral cavity, a safe and effective amount of the oral composition of the present invention.

The oral composition of the present invention includes an antibacterial effective amount of cetylpyridinium chloride typically in the range of from about 0.01 to 1.0% by weight, preferably from about 0.1 to 0.75% by weight, and other oral care components which do not materially prevent cetylpyridinium chloride from binding to tooth surfaces to perform an antibacterial function. A typical toothpaste composition may contain 0.5% by weight of cetylpyridinium chloride while a typical mouthwash composition may contain 0.125% by weight. The phrase "do not materially prevent" as used herein means that a sufficient amount of cetylpyridinium chloride is and remains available to bind to oral surfaces including tooth surfaces to perform an effective antibacterial function in the oral cavity.

The oral compositions of the present invention may be in the form of mouthwashes, gargles, dentifrices, anti-plaque compositions and as a general antiseptic composition, for example, in the form of denture cleansing tablets or solutions. Such oral compositions contain a number of components which have an active oral hygiene function or provide the compositions with a supporting function and do not interfere with the function of the active components. Examples of active components are tooth whiteners, antibacterial agents, abrasives or polishing materials, desensitizing agents, and the like. Examples of supporting components include organic surfactants which assist in the thorough and complete dispersion of one or more active agents, orally acceptable carriers, sweetening agents, preservatives, humectants, thickeners, and the like. The organic surfactants may and usually do provide both active cleaning as well as supporting functions.

The oral composition of the present invention may be in the form of a solution such as a mouthwash, a denture cleanser, a gargle or the like, or may be in the form of a semi-solid or solid such as a toothpaste, a gel dentifrice, a dental powder, a denture cleansing tablet, a chewing gum, or a solid lozenge or the like.

Cetylpyridinium chloride is cationic and therefore is attracted to negative surfaces and moieties. Tooth surfaces typically have a negative charge and therefore there is a natural attraction of cetylpyridinium chloride for tooth surfaces. However, many conventional oral care products contain components, including those found in toothpaste, which are anionic. Such negatively charged components bind to cetylpyridinium chloride and therefore make the antibacterial agent less available for binding to tooth surfaces and microorganisms.

In accordance with one aspect of the present invention, it has been discovered that the employment of guar hydroxypropyltrimonium chloride at least reduces and may substantially eliminate the ability of such compounds to bind to and diminish the antibacterial activity of cetylpyridinium chloride.

By way of example, certain sweetening agents known for use in oral compositions, such as saccharin, acesulfame, and cyclamate have been found to bind to and thereby inhibit the antibacterial activity of cetylpyridinium chloride when compared to compositions which do not contain such particular sweetening agents. In the oral composition of the present invention, the presence of typical sweetening agents does not adversely affect the antibacterial activity of cetylpyridinium chloride when guar hydroxypropyltrimonium chloride is present in effective amounts.

Guar hydroxypropyltrimonium chloride, available from several companies including Aqualon Corp. (a division of Hercules, Inc.), Cognis Corp., and Rhodia Inc., is a moisture-retaining polymer derived from guar gum and is useful as an antistatic agent, a hair conditioning agent, and an aqueous viscosity enhancing agent for use in soaps, hair care and skin care products. Guar hydroxypropyltrimonium chloride is also marketed under the trade name "N-Hance 3215" by Hercules Incorporated, Wilmington, Del.

The present invention also provides a method of reducing the presence of microorganisms in a oral cavity comprising administering to the oral cavity an effective amount of an oral composition comprising an antibacterial effective amount of cetylpyridinium chloride and an effective amount of guar hydroxypropyltrimonium chloride. The present oral composition enables cetylpyridinium chloride to effectively bind to the tooth surfaces to perform an antibacterial function.

Guar hydroxypropyltrimonium chloride is incorporated into the oral composition of the present invention in an effective amount which is sufficient to bind to compounds which have the ability to bind to cetylpyridinium chloride. If a sufficient amount of such compounds can no longer bind to the antibacterial agent, then a sufficient amount of cetylpyridinium chloride will be available to perform its antibacterial function. Generally, guar hydroxypropyltrimonium chloride will be present in an amount of from about 0.1 to 3.0% by weight of the total weight of the oral composition, preferably from about 0.4 to 2.5% by weight. A typical toothpaste composition may contain 2% by weight while a typical mouthwash composition may contain 0.5% by weight of the guar hydroxypropyltrimonium chloride.

The concentration of cetylpyridinium chloride and guar hydroxypropyltrimonium chloride will depend, in part, on the form of the composition (i.e. a solution such as mouthwash or gargle or a semi-solid such as a toothpaste, lozenge, and chewing gum) which is used to deliver cetylpyridinium chloride to the gingiva/muscosal tissue and/or the tooth surfaces. For example, solutions containing cetylpyridinium chloride are generally more efficient in contacting the tissue and tooth surfaces than semi-solid compositions and therefore may require a lower concentration of the antibacterial agent.

Orally acceptable carriers are typically present in the oral composition of the present invention. The term "orally acceptable carrier" as used herein is meant to include one or more compatible solid or liquid filler diluents or encapsulating substances which are suitable for topical, oral administration. It is understood that the components of the composition are preferably capable of being commingled without interaction in a manner which would substantially reduce the composition's stability and/or efficacy for reducing the presence of microorganisms in the oral cavity according to the compositions and methods of the present invention. The orally acceptable carriers of the present invention can include the usual and conventional components of toothpastes (including pastes, gels and gels for subgingival application), mouthwashes, mouth sprays, gargles, denture cleansers, chewing gums, and lozenges (including breath mints). Such orally acceptable carriers include, but not limited to, water, oils, organic solvents, saline, alcohols such as ethanol, glycerin, waxes, soft paraffin bases, petrolatum, lanolin, mixtures thereof and the like. The orally acceptable carrier will vary according to the form of the composition and is typically present in an amount of from about 20 to 99% by weight. A typical toothpaste composition may contain 15% glycerol and 20% water. A typical mouthwash composition may contain 94% of the sum of water, alcohol, and glycerin.

The choice of the orally acceptable carrier to be used is basically determined by the way the composition is to be administered to the oral cavity of the warm-blooded animal. Carriers suitable for the preparation of compositions of the present invention are well known in the art. Their selection may also depend in part on other considerations such as organoleptic properties including taste and mouth texture, cost, shelf stability, and the like.

Where the oral composition of the present invention is a gel or paste such as in a toothpaste (dentifrice), dental cream dentifrices or gel dentifrices, an orally acceptable carrier, including a water-phase with humectant which is preferably glycerin or sorbitol or an alkylene glycol such as polyethylene glycol or propylene glycol may be present. Such gel or paste compositions typically further contain a natural or synthetic thickener or gelling agent.

Where the oral composition of the present invention is a solution or a liquid such as a mouthwash, the orally acceptable carrier is typically a water-alcohol mixture.

Generally, the weight ratio of water to alcohol is in the range of from about 3:1 to 20:1 and preferably from about 4:1 to 10:1. The alcohol may include a non-toxic alcohol such as ethanol or isopropanol. A humectant such as glycerin, sorbitol or an alkylene glycol such as polyethylene glycol or preferably propylene glycol may also be present.

The mouthwash form of the oral composition may be suitably prepared by mixing the appropriate components thereof. Dentifrices are prepared in a similar manner with the addition, typically, of a thickener and a polishing agent.

The oral compositions of the present invention may be incorporated into solids such as lozenges, or in chewing gum or other products, e.g. by stirring into a warm gum base or coating the outer surface of a gum base, illustrative of which may be mentioned jelutone, rubber latex, vinylite resins, and the like, desirably with conventional plasticizers or softeners, sugar or other sweeteners or carbohydrates such as glucose, sorbitol and the like. The orally acceptable carrier for a tablet or lozenge is desirably a non-cariogenic solid water-soluble polyhydric alcohol (polyol) such as mannitol, xylitol, sorbitol, maltitol, a hydrogenated starch hydrolysate, Lycasin, hydrogenated glucose, hydrogenated disaccharides or hydrogenated polysaccharides. Solid salts such as sodium bicarbonate, sodium chloride, potassium bicarbonate or potassium chloride may totally or partially replace the polyol carrier. Tableting lubricants may be further incorporated into the tablet or lozenge formulation to facilitate the preparation of both the tablets and lozenges. Suitable lubricants include vegetable oils such as coconut oil, magnesium stearate, aluminum stearate, talc, starch and Carbowax ® sold by Union Carbide Corporation.

Lozenge formulations contain about 2% gum as a barrier agent to provide a shiny surface as opposed to a tablet which has a smooth finish. Suitable non-cariogenic gums include kappa carrageenan, carboxymethyl cellulose, hydroxyethyl cellulose, and the like. The lozenge or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth.

The present oral composition may optionally contain a sweetening agent for masking the objectionable taste often associated with cetylpyridinium chloride and improving the organoleptic properties of the oral composition. Suitable sweetening agents include high potency sweeteners such as cyclamate, saccharine, acesulfame, and sucralose, and the orally acceptable salts thereof, and bulk sweeteners such as xylitol, sorbitol, erythritol. Additional sweeteners such as sucrose, lactose, maltose, glucose, and fructose may also be used, but are not desirable due to their carriogenic potential.

The high potency sweeteners are typically utilized in amounts of from about 0.05% to 2% by weight based on the total weight of the composition while bulk sweeteners are used in amounts of from about 2 to 15% by weight. Typically, the high potency sweeteners are used in toothpastes in amounts of from about 0.1 to 1.5%, preferably from about 0.75 to 1.25%, most preferably about 1%. In mouthwashes, the high potency sweeteners are typically used in amounts of from about 0.05% to 0.25%, preferably from about 0.07% to about 0.12%, most preferably about 0.1% by weight. The bulk sweeteners are typically used in toothpastes in amounts of from about 10 to 40%, preferably from about 25 to 35%, most preferably about 30% by weight. In mouthwashes, the bulk sweeteners are typically used in amounts of from about 2 to 15% by weight, preferably from about 8 to 12%. Lower amounts of each of these may be used if multiple sweetening agents are used.

Antibacterial agents other than cetypyridinium chloride may be optionally present in the oral compositions of the present invention. Such agents may include, but not limited to, chlorhexidine gluconate; benzalkonium chloride; benzethonium chloride; domiphen bromide; zinc salts such as zinc chloride, citrate or gluconate; stannous salts such as stannous chloride and fluoride; triclosan; sanguinarine chloride; and essential oils such as eucalyptol, thymol, menthol and eugenol. If present, the additional antibacterial agents generally comprise up to about 2% by weight, preferably from about 0.1 to 2% by weight of the composition of the present invention.

Further other components can be suitably incorporated within a range that the action and effect of the present invention are not diminished or lessened.

Other components which may be incorporated into the oral composition of the present invention include, but not limited to, thickening agents, whiteners, flavorants, humectants, desensitizing agents, abrasives, fluoride supplying compounds, coloring agents and the like. Suitable non-ionic thickening agents include ($C_{2-6}$) alkylene oxide modified ($C_{1-6}$) alkylcellulose ethers such as hydroxyethylcellulose, hydroxypropylcellulose, hydroxypropylmethylcellulose, and mixtures thereof. Suitable cationic thickening agents include quaternary cellulose derivatives, and the like. The thickening agents are typically present in an amount of from about 0.1 to 3% by weight.

Abrasive agents include certain phosphates such as sodium metaphosphate, potassium metaphosphate, tricalcium phosphate, dicalcium phosphate dihydrate, anhydrous dicalcium phosphate, calcium pyrophosphate, zinc orthophosphate, alumina, hydrated alumina, aluminum silicate, bentonite, calcium carbonate, sodium bicarbonate and the like. The abrasive agents are typically present in an amount of from about 0.5 to 70% by weight, preferably from about 5 to 40% by weight based on the total weight of the composition.

Fluoride-supplying compounds include inorganic fluoride salts, such as soluble alkali metal, alkaline earth metal, and heavy metal fluoride salts, for example, sodium fluoride, potassium fluoride, ammonium fluoride, lead fluoride, copper fluoride, zinc fluoride, tin fluoride, barium fluoride, sodium fluorosilicate, ammonium fluorosilicate, sodium fluorozirconate, sodium monofluorophosphate, and the like. The fluoride-supplying compound is typically present in an amount sufficient to deliver from about 50 to 5,000 ppm, preferably from about 100 to 2,500 ppm, more preferably from about 1,000 to 1,200 ppm of available fluoride based on the composition.

Humectants suitable for use in the present oral composition include glycerin, sorbitol, alkylene glycols such as polyethylene glycol or preferably propylene glycol, and the like. The humectant is typically present in an amount of from about 1 to 50% by weight, preferably from about 5 to 30% by weight based on the total weight of the composition.

Desensitizing agents include potassium salts, and strontium salts especially potassium nitrate, strontium chloride, potassium citrate, and the like. The desensitizing agent is typically present in an amount sufficient to provide an effective amount of the potassium or strontium ion. For potassium nitrate, 5% by weight is a typical standard amount. Generally a greater amount of the strontium compound is required than the potassium compound.

The present invention may also include an alkali metal bicarbonate salt. Alkali metal bicarbonate salts are soluble in water and unless stabilized, tend to release carbon dioxide in an aqueous system. Sodium bicarbonate is the preferred alkali metal bicarbonate salt. The present composition may contain up to about 75% by weight, preferably from about 5 to 40% by weight of an alkali metal bicarbonate salt.

In accordance with a preferred aspect of the present invention, a cetylpyridinium chloride-containing toothpaste composition containing guar hydroxypropyltrimonium chloride alone or in combination with a sweetening agent, especially sodium saccharin dihydrate provides significant availability of the antibacterial agent to bind to tooth surfaces.

A safe and effective amount of the compositions of the present invention may be topically applied in several conventional ways to the mucosal tissue of the oral cavity, to the gingival tissue of the oral cavity, and/or to the tooth surface, for reducing the levels of undesirable oral microorganisms residing thereon. For example, the gingival or mucosal tissue may be rinsed with a solution (e.g., mouthwash, mouth spray) containing cetylpyridinium chloride and guar hydroxypropyltrimonium chloride, or if cetylpyridinium chloride and guar hydroxypropyltrimonium chloride are included in a dentifrice (e.g., toothpaste, tooth gel, or tooth powder), the gingival or mucosal tissue is bathed in the liquid and/or in the lather generated by brushing of the teeth.

Other non-limiting examples include applying a non-abrasive gel or paste, which contains cetylpyridinium chloride and guar hydroxypropyltrimonium chloride, directly to the gingival/mucosal tissue or to the tooth surface with or without an oral care implement; chewing gum that contains cetylpyridinium chloride and guar hydroxypropyltrimonium chloride; chewing or sucking on a breath tablet or lozenge which contains cetylpyridinium chloride and guar hydroxypropyltrimonium chloride. Preferred methods of using compositions of the present invention include applying cetylpyridinium chloride and guar hydroxypropyltrimonium chloride to the gingival/mucosal tissue and/or the tooth surface via rinsing with a mouthwash solution and via brushing with a dentifrice. Other methods of applying cetylpyridinium chloride and guar hydroxypropyltrimonium chloride to the gingival/mucosal tissue and tooth surfaces are apparent to those skilled in the art.

The foregoing discussion discloses and describes merely exemplary embodiments of the present invention. One skilled in the art will readily recognize from such discussion, and from the accompanying examples and claims, that various changes, modifications and variations can be made therein without departing from the spirit and scope of the invention as defined in the following claims.

EXAMPLE 1

Effect of Guar Hydroxypropyltrimonium Chloride on Adsorption of Cetylpyridinium Chloride in the Presence of a Sweetening Agent In vitro studies of cetylpyridinium chloride absorption were performed with the initial step of formulating a model oral surface. Disks of hydroxyapatite (HAP, calcium phosphate hydroxide, $Ca_{10}(PO_4)_6(OH)_2$) measuring 0.5 inch diameter and 0.04 inch thick were obtained from Clarkson Chromatography Products (Williamsport, Pa.). The disks were hydrated in deionized water for one hour and then allowed to air dry.

A 1% dispersion of bovine submaxillary mucin (type 1S, from Sigma) in water was then prepared. The HAP disks were soaked in the 1% mucin dispersion overnight. The HAP disks were then allowed to air dry for at least 3 hours. The disks comprising HAP on which was deposited a layer of mucin, represented an oral surface.

Cetylpyridinium chloride adsorption was tested by soaking the disks in a test solution. The compositions of the test solutions are shown and listed in Table 1. Guar hydroxypropyltrimonium chloride was obtained from Hercules Incorporated, Wilmington, Del., which is marketed under the trade name "N-Hance 3215". The disks were each soaked in 5 mL of the test solution for 10 minutes in a polystyrene petri dish (35 mm diameter×10 mm deep, from Becton Dickson). The disks were then removed, rinsed for 3 seconds with deionized water on each side with a wash bottle.

Adsorbed cetylpyridinium chloride was extracted by soaking the disks in a solution used as a mobile phase for cetylpyridinium chloride detection in liquid chromatography. The extractant solution was composed of 60 parts of a 20 mM phosphate buffer and 40 parts methanol, in which was dissolved 30 mM cetyltrimethylammonium bromide (CTAB). The disks were soaked in 5 mL of the extractant solution for 2 hours. The extractant was then analyzed for cetylpyridinium chloride using high-pressure liquid chromatography.

The composition of each test solution and the results of cetylpyridinium chloride absorption tests are shown in Table 1.

TABLE 1

| Test Solutions | % by Weight of Guar hydroxypropyltrimonium chloride | % by Weight of Sodium saccharin dihydrate | % by Weight of CPC. $1H_2O$ | % by Weight of 0.125% $NaHCO_3$ in Aq. solution | CPC Adsorbed (µg/disk) |
|---|---|---|---|---|---|
| A | — | — | 0.125 | q.s. to 100 | 32.4 ± 6.5 |
| B | — | 0.075 | 0.125 | q.s. to 100 | 8.0 ± 1.6 |
| C | 0.5 | — | 0.125 | q.s. to 100 | 25.1 ± 5.0 |
| D | 0.5 | 0.075 | 0.125 | q.s. to 100 | 16.3 ± 3.2 |

As shown in Table 1, the addition of guar hydroxypropyltrimonium chloride to a solution containing saccharin increased the adsorption of cetylpyridinium chloride by about a factor of at least two as compared to the solution containing only cetylpyridinium chloride and saccharin.

EXAMPLE 2

Effect of Guar Hydroxypropyltrimonium Chloride on Adsorption of Cetylpyridinium Chloride in the Presence of an Emollient In vitro studies of cetylpyridinium chloride adsorption were performed with the initial step of formulating a model oral surface. Disks of hydroxyapatite (HAP, calcium phosphate hydroxide, $Ca_{10}(PO_4)_6(OH)_2$) measuring 0.5 inch diameter and 0.04 inch thick were obtained from Clarkson Chromatography Products (Williamsport, Pa.). The disks were hydrated in deionized water for one hour and then allowed to air dry.

A 1% dispersion of bovine submaxillary mucin (type 1S, from Sigma) in water was then prepared. The HAP disks were soaked in the 1% mucin dispersion overnight. The HAP disks were then allowed to air dry for at least 3 hours. The disks comprising HAP on which was deposited a layer of mucin, represented an oral surface.

Cetylpyridinium chloride absorption was tested by soaking the disks in a test solution. The test solutions are shown and listed in Table 2. Guar hydroxypropyltrimonium chloride was obtained from Hercules Incorporated, Wilmington, Del., which is marketed under the trade name "N-Hance 3215". Eldew CL-301 or cholesteyrl/behenyl/octyldecyl lauroyl glutamate, is an emollient derived from L-glutamic acid, lauric acid and three alcohols (cholesterol, 2-octyldodecanol, and behenol), and is marketed and manufactured by Ajinomoto Inc. (Tokyo, Japan). The disks were each soaked in 5 mL of the test solution for 10 minutes in a polystyrene petri dish (35 mm diameter×10 mm deep, from Becton Dickson). The disks were then removed, rinsed for 3 seconds with deionized water on each side with a wash bottle.

Adsorbed cetylpyridinium chloride was extracted by soaking the disks in a solution used as a mobile phase for cetylpyridinium chloride detection in liquid chromatography. The extractant solution was composed of 60 parts of a 20 mM phosphate buffer and 40 parts methanol, in which was dissolved 30 mM cetyltrimethylammonium bromide (CTAB). The disks were soaked in 5 mL of the extractant solution for 2 hours. The extractant was then analyzed for cetylpyridinium chloride using high-pressure liquid chromatography.

The composition of each test solution and the results of cetylpyridinium chloride adsorption tests are shown in Table 2.

TABLE 2

| Test Solutions | % by Weight % of guar hydroxypropyltrimonium chloride | % by Weight of Eldew CL-301 | % by Weight of CPC. 1H$_2$O | % by Weight of 0.125% NaHCO$_3$ in aqueous solution | CPC Adsorbed ($\mu$g/disk) |
|---|---|---|---|---|---|
| E | — | — | 0.125 | q.s. to 100 | 41.0 ± 8.2 |
| F | — | 2.0 | 0.125 | q.s. to 100 | 4.9 ± 1.0 |
| G | 0.5 | 2.0 | 0.125 | q.s. to 100 | 20.9 ± 4.2 |

As shown in Table 2, the addition of guar hydroxypropyltrimonium chloride to a solution containing Eldew CL-301 increased the adsorption of cetylpyridinium chloride by about a factor of at least four as compared to the solution containing only cetylpyridinium chloride and Eldew CL-301.

What is claimed is:

1. An oral composition comprising:
   a) an antibacterial effective amount of cetylpyridinium chloride;
   b) an effective amount of guar hydroxypropyltrimonium chloride, sufficient to bind to compounds which undesirably bind to cetylpyridinium chloride thereby enabling the cetylpyridinium chloride to effectively bind to tooth surfaces and perform an antibacterial function; and
   c) an orally acceptable carrier.

2. The oral composition of claim 1, wherein the orally acceptable carrier is selected from the group consisting of water, saline, alcohol, glycerin, oil and mixtures thereof.

3. The oral composition of claim 1, wherein the oral composition is in a form selected from the group consisting of a mouthwash, a dentifrice, a chewing gum, and a lozenge.

4. The oral composition of claim 1, the amount of cetylpyridinium chloride is present from about 0.01 to 1.0% by weight based on the total weight of the oral composition.

5. The oral composition of claim 1, wherein the amount of guar hydroxypropyltrimonium chloride is present from about 0.1 to 3.0% by weight based on the total weight of the oral composition.

6. The oral composition of claim 3 wherein the dentifrice is a toothpaste.

7. The oral composition of claim 6 further comprising at least one material selected from the group consisting of thickening agents, whiteners, flavorants, humectants, desensitizing agents, abrasive agents, alkali metal bicarbonate salts, and fluoride supplying compounds.

8. The oral composition of claim 7 wherein the abrasive agents are selected from the group consisting of sodium metaphosphate, potassium metaphosphate, tricalcium phosphate, dicalcium phosphate dihydrate, anhydrous dicalcium phosphate, calcium pyrophosphate, zinc orthophosphate, alumina, hydrated alumina, aluminum silicate, bentonite, calcium carbonate, and sodium bicarbonate.

9. The oral composition of claim 1 further comprising at least one sweetening agent.

10. The oral composition of claim 9 comprising at least one high potency sweetening agent.

11. The oral composition of claim 1 further comprising at least one additional antibacterial agent.

12. The oral composition of claim 11 wherein the at least one additional antibacterial agent is present in an amount of from about 0.1 to 2% by weight based on the total weight of the oral composition.

13. The oral composition of claim 7 wherein the abrasive agent is present in an amount of from about 0.5 to 70% by weight.

14. The oral composition of claim 7 wherein the fluoride supplying compound is present in an amount sufficient to deliver from about 100 to 5,000 ppm of available fluoride based on the composition.

15. The oral composition of claim 7 wherein the alkali metal bicarbonate salts are present in an amount of up to about 75% by weight based on the total weight of the oral composition.

16. The oral composition of claim 15 wherein the amount of the alkali metal bicarbonate salts are present in an amount of from about 5 to 40% by weight.

17. The oral composition of claim 7 wherein the thickening agent is present in an amount of from about 0.1 to 3.0% by weight based on the total weight of the composition.

18. The oral composition of claim 1 wherein the orally acceptable carrier is present in an amount of from about 20 to 99% by weight based on the total weight of the composition.

19. The oral composition of claim 7 wherein the humectant is present in an amount of from about 1 to 50% by weight based on the total weight of the composition.

20. A method of reducing the presence of microorganisms in an oral cavity of a warm-blooded animal, said method comprising administering to the oral cavity an effective amount of the oral composition of claim 1.

* * * * *